US00PP36805P3

(12) United States Plant Patent
Bourne

(10) Patent No.: US PP36,805 P3
(45) Date of Patent: Jul. 8, 2025

(54) GRAPEVINE NAMED 'SV35-179-125'

(50) Latin Name: *Vitis vinifera*
Varietal Denomination: SV35-179-125

(71) Applicant: Sunview Vineyards of California, Inc., Delano, CA (US)

(72) Inventor: Timothy F Bourne, Visalia, CA (US)

(73) Assignee: Sunview Vinyards of California, Inc., Delano, CA (US)

( * ) Notice: Subject to any disclaimer, the term of this patent is extended or adjusted under 35 U.S.C. 154(b) by 0 days.

(21) Appl. No.: 18/831,169

(22) Filed: Aug. 26, 2024

(65) Prior Publication Data

US 2025/0081868 P1 Mar. 6, 2025

Related U.S. Application Data

(60) Provisional application No. 63/628,958, filed on Sep. 5, 2023.

(51) Int. Cl.
*A01H 5/08* (2018.01)
*A01H 6/88* (2018.01)

(52) U.S. Cl.
USPC ..... Plt./205
CPC ..... *A01H 6/88* (2018.05)

(58) Field of Classification Search
USPC ..... Plt./205
CPC ..... A01H 6/88; A01H 5/08
See application file for complete search history.

*Primary Examiner* — Keith O. Robinson

(74) *Attorney, Agent, or Firm* — Eric C. Cole; Baker Manock & Jensen, PC

(57) ABSTRACT

A new and distinct variety of grapevine plant named 'SV35-179-125' particularly characterized by its black, early ripening fruit with muscat flavor and which ripen in mid to late July in the McFarland, California area.

2 Drawing Sheets

Latin name of the genus and species of the plant claimed: The plant claimed relates to a new and distinct variety of *Vitis vinifera*.

Variety denomination: The plant claimed shall be known as 'SV35-179-125'.

STATEMENT OF ANY FEDERALLY-SPONSORED RESEARCH AND DEVELOPMENT

The present invention is not subject of Federally-sponsored research or development.

BACKGROUND OF THE INVENTION

The present invention comprises a new and distinct cultivar of grapevine botanically known as *Vitis vinifera* and hereinafter referred to as grapevine named 'SV35-179-125'. As used herein, 'grapevine' refers to all plant parts including, vines, canes, tendrils, leaves, fruit and roots of 'SV35-179-125'. Grapevine named 'SV35-179-125' is the result of an effort to produce an early ripening, black, seedless table grape with fruit characteristics superior to currently available green grape cultivar 'Summer Royal' (unpatented). This new cultivar originated from a cross conducted in May 2014 near McFarland, California between female grapevine plant selection 'SV16-72-83' (unpatented) and pollen parent grapevine 'SV21-66-158' (U.S. Plant Pat. No. 24,510). Resultant ovules from the cross were harvested 42 days after pollination and cultured on 'McCown's Woody Plant Medium'. Subsequently, the resultant embryonic plants were cultured in the same medium in the laboratory under twelve hours of light from light emitting diodes at 29° C. The seedlings from this effort were transplanted to the greenhouse in November of 2014 and grown in the greenhouse at 29° C. with 12 hours illumination under high pressure sodium vapor lamps. The seedling population of 90 plants was planted in the field in the spring of 2015 near McFarland, California. The new grapevine was selected from this seedling population on Jul. 2, 2016. It was then propagated by cuttings and bench grafted to 'Freedom' (unpatented) rootstock in 2017. The present invention has been found to retain its distinctive characteristics through two successive asexual propagations.

Grapevine named 'SV35-179-125' differs from its female parent grapevine 'SV16-72-83' (unpatented) in that 'SV35-179-125' has ovate shaped, seedless berries whereas 'SV16-72-83' has spherical shaped berries with partially lignified seed traces.

Grapevine named 'SV35-179-125' differs from its male parent grapevine 'SV21-66-158' (U.S. Plant Pat. No. 24,510) in that 'SV35-179-125' has ovate shaped, black berries whereas 'SV21-66-158' has cylindrical shaped green berries.

Grapevine named 'SV35-179-125' differs from the commercial cultivar 'Summer Royal' (unpatented) by producing berries which are ovate as opposed to spherical. While both cultivars ripen early in the season, 'SV35-179-125' has berries with a mild muscat flavor while 'Summer Royal' berries have no muscat flavor.

Grapevine Named 'SV35-179-125' is most similar to commercially available cultivar 'Fantasy Seedless' (unpatented). Grapevine Named 'SV35-179-125' differs from 'Fantasy Seedless' by ripening in early July versus September for 'Fantasy Seedless' (unpatented) in the McFarland, California area. Grapevine named 'SV35-179-125' also produces large, well-filled clusters of berries whereas 'Fantasy Seedless' often produces clusters which are not completely filled with berries and having naked rachises.

SUMMARY OF THE INVENTION

The following are the most outstanding and distinguishing characteristics of the ripe fruit of this new variety when grown under normal horticultural practices near McFarland, California:

a. Black skinned berries.
b. Firm berry texture; and
c. Large, ovate shaped berries with slight muscat flavor.

BRIEF DESCRIPTION OF THE DRAWINGS

This new grapevine is illustrated by the accompanying photographs which show fruit clusters, leaves, canes and tendrils. The colors shown are as true as can be reasonably obtained by conventional photographic procedures. The photographs were taken from a plant about 5 years-old, grown in a field near McFarland, California in 2021.

DETAILED BOTANICAL DESCRIPTION

Figure 1:
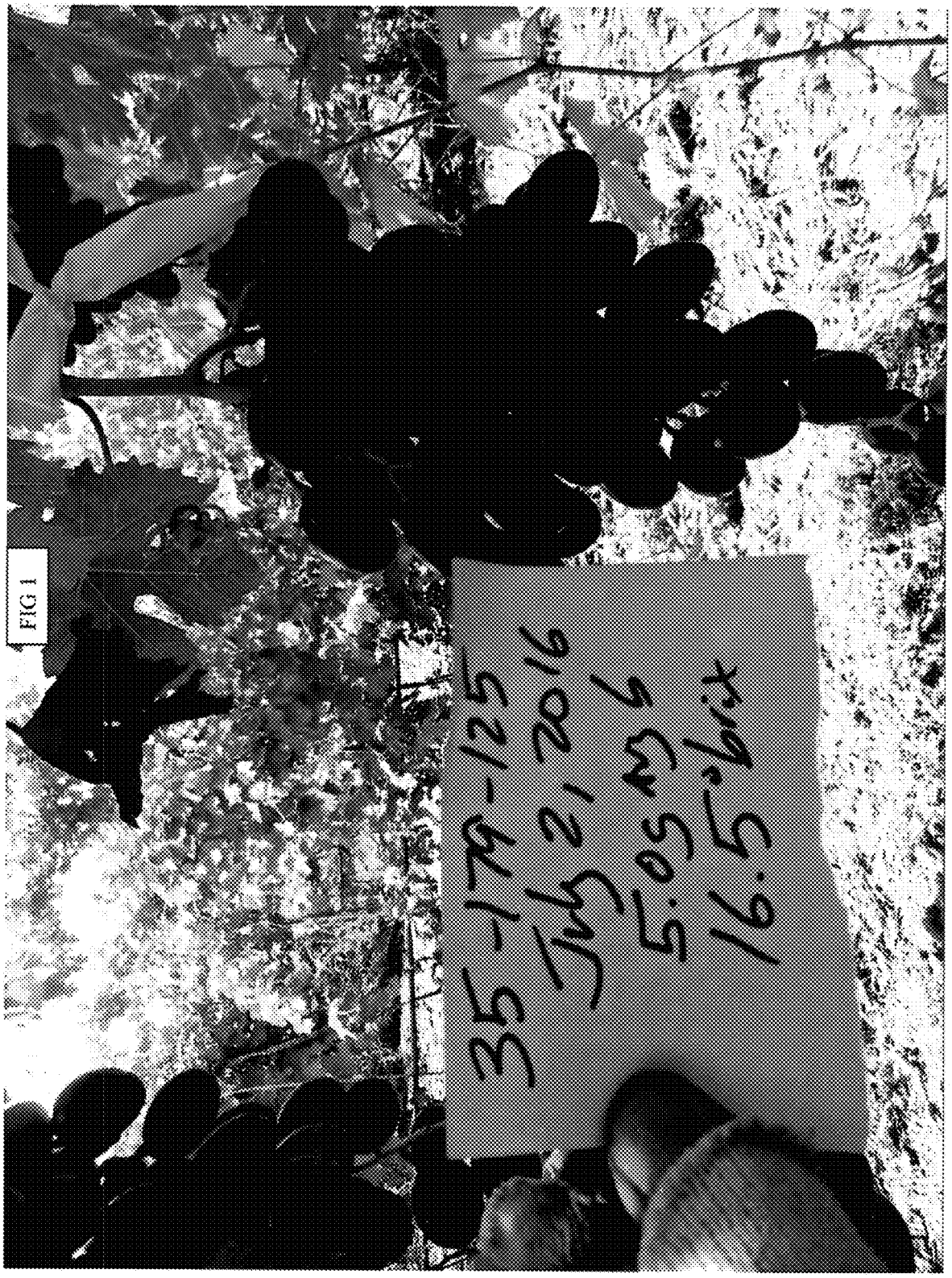
FIG. 1 Fruit clusters on the vine of grapevine named 'SV35-179-125'.
Figure 2:
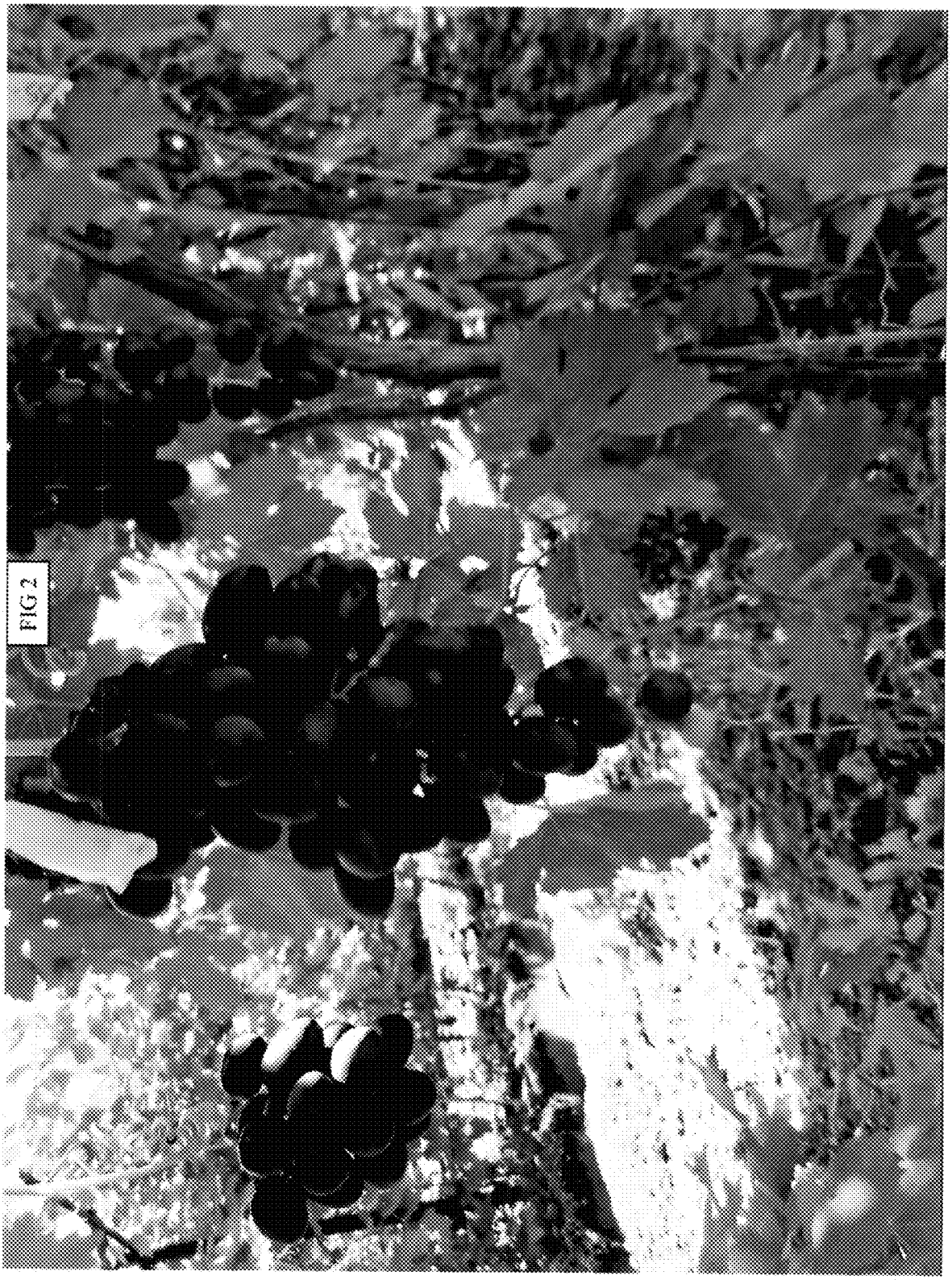
FIG. 2 Fruit clusters on the vine of grapevine named 'SV35-179-125'.

The following detailed description sets forth the distinctive characteristics of grapevine named 'SV35-179-125'. Descriptions of the new invention apply to vines of grapevine named 'SV35-179-125' grown on 'Freedom' (unpatented) rootstock at a density of 1,537 vines per hectare grown near McFarland, California in 2011. These vines were in their fifth year of full production having been planted in 2016. These descriptions are believed to apply generally to the new variety grown under similar circumstances elsewhere. Color references are to The Royal Horticultural Society's Colour Chart, The Royal Horticultural Society, London, United Kingdom (copyright 2001). Descriptors used herein conform to those set forth by the International Board for Plant Genetic Resources Institute Grape Descriptors (*Vitis* spp.) of 1983 and/or 1997 which were developed in collaboration with the Office Interantional de la Vigne et du Vin (OIV) and the International Union for the Protection of New Varieties of Plants (UPOV) and published in *Descriptors for Grapevine* (*Vitis spp.*) (Anonymous, International Plant Genetic Resources Institute, 1997, ISBN 92-9043-352-3).

Classification:
- *Family*.—Vitaceae.
- *Botanical name*.—*Vitis vinifera*.
- *Variety name*.—'SV35-179-125'.

Plant:
- *Density of foliage*.—Moderate.
- *Productivity*.—Very productive when spur pruned, up to 39,329 kg/hectare.
- *Hardiness*.—Hardiness observed to 0° C.
- *Rootstock*.—'Freedom' (unpatented).
- *Vigor*.—Vines spur pruned and shoot thinned to 32 shoot average 180.94 cm of growth per cane.
- *Bud burst*.—Early.

Trunk:
- *Shape*.—Broadly elliptical.
- *Straps*.—Long, split.
- *Surface texture*.—Shaggy.
- *Trunk circumference*.—21.3 cm at 1.0 m of height.
- *Inner bark color*.—RHS greyed-orange group 175A.
- *Outer bark color*.—RHS brown group 200C.

Mature leaves:
- *Average blade length*.—16.3 cm.
- *Average blade width*.—22.4 cm.
- *Size of blade*.—Large.
- *Shape*.—Pentagonal.
- *Number of lobes*.—5.
- *Anthocyanin coloration of main veins on the upper side of the blade*.—Absent.
- *Mature leaf profile*.—Cupped upwards around entire margin.
- *Blistering* (*upper surface*).—Absent.
- *Leaf blade tip*.—Apiculate.
- *Margins*.—Lobed, serrated, undulating.
- *Apex*.—Broadly acuminate.
- *Bases*.—Sagittate.
- *Thickness*.—Medium.
- *Undulation of blade between main and lateral veins*.—Slight.
- *Shape of teeth*.—Broadly conical, both sides convex.
- *Length of teeth*.—7.2 mm.
- *Ratio length/width of teeth*.—7.2-9.9.
- *General shape of petiole sinus*.—Wide open.
- *Tooth at petiole sinus*.—Absent.
- *Petiole sinus limited by veins*.—Absent.
- *Shape of upper lateral sinus*.—Open.
- *Prostrate hairs between veins* (*lower surface*).—Sparse.
- *Erect hairs between veins* (*lower surface*).—Moderately abundant.
- *Prostrate hairs on main veins* (*lower surface*).—Very sparse.
- *Density of erect hairs on main veins* (*lower surface*).—Sparse.
- *Prostrate hairs on main veins* (*upper surface*).—Absent.
- *Upper surface*.—Summer color: RHS yellow-green group 147A. Surface texture: Smooth. Surface appearance: Dull. Goffering of blade: Absent.
- *Lower surface*.—Summer color: RHS green group 137C. Anthocyanin coloration of main veins on lower leaf surface: Absent. Anthocyanin coloration on laterals: Absent. Glossiness: Low. Surface texture: Rough. Surface appearance: Dull.
- *Petiole*.—Length: 13.5 cm. Length of petiole compared to middle vein: Slightly shorter. Density of prostrate hairs: Absent. Density of erect hairs: Absent. Shape of base of petiole sinus: Wide open. Color: In shade: RHS yellow-green group 146C. In sun: RHS yellow-green group 144C.

Tendrils:
- *Number*.—Bifurcated and trifurcated; Alternating after 6th node.
- *Length*.—26.8 cm.
- *Diameter*.—2.8 mm.
- *Texture*.—Smooth.
- *Color*.—RHS yellow-green group 144A.

Growing tips (young shoot):
- *Pubescence*.—Present, prostrate.
- *Color*.—RHS Yellow green group 144A.
- *Anthocyanins*.—Present.
- *Shape*.—Rounded.
- *Apex*.—Fully open.

*Shoot attitude*.—Semi-erect.
*Prostrate hairs*.—Very sparse.
*Anthocyanin coloration on prostrate hairs*.—Very weak.

Green summer shoots:
*Internode color upper surface*.—RHS brown group 200D.
*Internode color lower surface*.—RHS yellow-green group 144B.
*Node color upper surface*.—RHS brown group 200D.
*Node color lower surface*.—RHS yellow-green group 144B.
*Density of erect hairs on internodes*.—Absent.

Woody shoot:
*Canes*.—Shape: Broadly elliptical. Internode length: 10.9 cm. Width at node: 15.0 mm. Surface: Smooth. Main color: RHS Greyed orange group 165C. Lenticels: Inconspicuous.
*Buds*.—Shape: Conical. Bud fruitfulness: Very fruitful. Most shoots bear two clusters when spur pruned. Length: 6.0 mm. Width: 4.4 mm. Height: 4.3 mm. Color: RHS Greyed orange group 166A. Texture: Smooth.

Flowers:
*Flower sex*.—Hermaphrodite.
*Position of first flowering nodes*.—4.
*Number of inflorescences per shoot*.—1 or 2.
*Flower cluster width*.—6.4 cm.
*Flower cluster length*.—27.5 cm.
*Cluster stem color*.—RHS Yellow-Green group 144B.
*Calyptra color*.—RHS Yellow-Green group 144A.
*Ovary length*.—2 mm.
*Ovary width*.—1 mm.
*Ovary color*.—RHS Green group 144B.
*Filament length*.—2 mm.
*Filament color*.—RHS Yellow-Green group 145C.
*Anther length*.—1 mm.
*Anther color*.—RHS Yellow group 13C.
*Date of full bloom*.—May 6, 2024.

Fruit:
*Ripening period*.—Mid July, Delano, California.
*Date of ripening*.—July 22, Delano, California.
*Use*.—Fresh market.
*Keeping quality*.—Very good.
*Shipping quality*.—Good.
*Date of first harvest*.—July 22.
*Solids-sugar*.—High, about 21 brix at full maturity.
*Refractometer test*.—21.5 brix.
*Bunch*.—Size: Large. Length (peduncle excluded): About 20.7 cm. Width: About 16.3 cm. Weight: Natural, without gibberellic acid treatment: 315 g. With gibberellic acid treatment: 340 g. Density: Well filled. Number of berries: Natural — 139 when treated with gibberllic acid: 77. Form: Conical.
*Peduncle*.—Length: About 6.1 cm. Lignification: None. Color: RHS yellow-green group N144D.
*Berry*.—Size: Large. Uniformity of size: Uniform. Weight: Natural, without gibberellic acid treatment: 4.0 g. With gibberellic acid treatment: 7.1 g. Shape: Natural, without gibberellic acid treatment: Ovate. With gibberellic acid treatment: Cylindrical. Presence of seeds: Seedless; most berries develop one or two small, soft rudimentary seeds less than 0.5 mm in length. Cross section: Circular. Dimensions: Longitudinal axis: 2.8 cm at base. Horizontal axis: 2.2 cm. Skin color (without bloom): RHS red-purple group 59A. Coloration of flesh: Translucent; yellow-green group 147D. Juiciness of flesh: Very juicy. Berry firmness: Medium firm. Particular flavor: Slight muscat. Bloom (cuticular wax): Slight. Pedicel length: 1.5 cm. Berry separation from pedicel: With difficulty.
*Skin*.—Thickness: Thin. Texture: Medium crisp. Reticulation: Absent. Roughness: Absent. Tenacity: Tenacious to flesh. Tendency to crack: Resistant.

Having thus described and illustrated our new variety of grapevine, I claim:

1. A new and distinct variety of grapevine plant named 'SV35-179-125', substantially as illustrated and described herein.

* * * * *